(12) United States Patent
Li et al.

(10) Patent No.: US 6,589,553 B2
(45) Date of Patent: Jul. 8, 2003

(54) CONTROLLED RELEASE ORAL DOSAGE FORM

(75) Inventors: Boyong Li, Davie, FL (US); Avinash Nangia, Weston, FL (US); Chih Ming Chen, Davie, FL (US)

(73) Assignee: Andrx Pharmaceuticals, Inc., Davie, FL (US)

( * ) Notice: Subject to any disclaimer, the term of this patent is extended or adjusted under 35 U.S.C. 154(b) by 203 days.

(21) Appl. No.: 09/905,712

(22) Filed: Feb. 8, 2001

(65) Prior Publication Data

US 2003/0054031 A1 Mar. 20, 2003

(51) Int. Cl.[7] .................................................. A61K 9/62
(52) U.S. Cl. ........................ 424/461; 424/459; 424/462; 424/494; 424/497
(58) Field of Search .................................. 424/459, 462, 424/461, 494, 497; 564/345

(56) References Cited

U.S. PATENT DOCUMENTS

| | | | | |
|---|---|---|---|---|
| 3,819,706 A | * | 6/1974 | Mehta et al. | 564/345 |
| 3,885,046 A | * | 5/1975 | Mehta et al. | 541/649 |
| 4,687,660 A | * | 8/1987 | Baker et al. | 424/465 |
| 5,358,970 A | * | 10/1994 | Ruff et al. | 514/649 |
| 5,427,798 A | * | 6/1995 | Ludwig et al. | 424/464 |

* cited by examiner

*Primary Examiner*—Samuel Barts
(74) *Attorney, Agent, or Firm*—Hedman & Costigan, P.C.

(57) ABSTRACT

A once a day bupropion hydrochloride formulation is disclosed.

8 Claims, 4 Drawing Sheets

US 6,589,553 B2

CONTROLLED RELEASE ORAL DOSAGE FORM

CROSS REFERENCE TO RELATED APPLICATIONS

The present invention is related to the application filed concurrently herewith U.S. application Ser. No. 09/905,690.

BACKGROUND OF THE INVENTION

1. Field of the Invention

The present invention relates to oral controlled release dosage formulations containing bupropion hydrochloride.

2. Description of the Related Art

The compound designated bupropion hydrochloride is described in U.S. Pat. Nos. 3,819,706 and 3,885,046. It is marketed as an antidepressant and an aid to smoking cessation. Bupropion is an aminoketone-derivative chemically unrelated to other currently available antidepressants (e.g., selective serotonin-reuptake inhibitors, tricyclics, tetracyclics).

While the neurochemical mechanisms of the antidepressant and smoking cessation effects are unknown, noradrenergic pathways and/or dopaminergic effects appear to be primarily involved. Bupropion does not inhibit monoamine oxidase and is a weak blocker of serotonin and norepinephrine uptake.

The drug is useful in the treatment of depressive affective disorders (e.g. major depression) at dosages of 75 to 600 mg daily. Bupropion may be preferable to other agents because of its minimal anticholinergic, cardiovascular, and antihistaminic effects or in those patients who have experienced weight gain or sexual dysfunction with another antidepressant. Bupropion, as extended-release tablets, is used in the cessation of smoking at dosages of 100–300 mg daily. Withdrawal symptoms and cigarette craving are reduced with bupropion. Other uses include patients with bipolar depression, attention-deficit hyperactivity in both adult and pediatric patients, and panic symptoms superimposed on depression.

Immediate release bupropion tablets provide more than 75% of bupropion release into the dissolution media in 45 minutes. In studies to date, the risk of seizures appears to be strongly associated, in part, with the use of instant release tablets.

Numerous techniques exist in the prior art for preparing sustained or controlled release pharmaceutical formulations. One common technique involves surrounding an osmotically active drug core with a semipermeable membrane. The drug is released from the core over time by allowing a fluid such as gastric or intestinal fluid to permeate the coating membrane and dissolve the drug so the dissolved drug can permeate the membrane. In some cases a hydrogel is employed to push the active ingredient through the passageway of the membrane.

Another common technique for preparing controlled-release pharmaceutical formulations is to encapsulate a plurality of beads, pellets or tablets that are coated with varying levels of diffusion barriers. Release of the pharmaceutical may occur by leaching, erosion, rupture, diffusion or similar actions depending on the nature and thickness of the coating material. These products require multi-layered coating, sometimes as much as 30 to 90 coats.

Film coating techniques are characterized by the deposition of a uniform film onto the surface of a substrate. Because of the capability of depositing a variety of coating materials onto solid cores, this process has been used to make controlled release dosage forms starting from different formulations, such as tablets, granules, pellets and capsules. Cores are usually prepared using one of the following processes: compaction, surface layering, or agglomeration.

One limitation associated with these dosage forms consists in their failure to delay drug delivery. Many of the multi-walled preparations described above do not provide prolonged delayed release of the drug prior to initiation of sustained release, which is important when biphaslc release profiles are desired. Other systems are essentially "delayed" release mechanisms. There is a delay of drug release in the stomach but once the coated drug reaches the intestines, the release of medication is rapid. There is no sustained release in the intestines.

Bupropion is highly soluble in water with a high permeability characterized by rapid and almost complete absorption. Peak plasma concentrations occur within 2 hours for bupropion and 3 hours for bupropion sustained-release. Its biphasic pharmacokinetics is characterized by a two-compartment model; the distributive phase has a mean half-life of 3 to 4 hours with a biphasic decline and a terminal T½ of about 14 hours following single doses. A major drawback is extensive first-pass metabolism. It appears that only a small portion of any oral dosage reaches the systemic circulation intact. Immediate-release tablets are dosed three times a day, preferably with 6 or more hours separating the doses. For those patients requiring doses greater than 300 mg daily, each divided dose should not exceed 150 mg each. This necessitates administration of the tablets 4 times daily with at least 4 hours between successive doses. Commercially available sustained-release products are available in film coated tablets marketed by Glaxo Wellcome under the trade names Wellbutrin® SR and Zyban.® These are dosed twice daily. For those patients requiring dosages above 300 mg daily, the regimen remains twice daily dosing. No currently commercially available product provides a sustained release profile suitable for once daily dosing.

Patient compliance is especially problematic in depressed patients. There is a need for improved patient compliance. One of the means employed clinically to improve patient adherence to therapy is simplification of the dosing regimen. Thus, need exists for a once daily bupropion formulation.

Sustained release tablet forms of bupropion are described in U.S. Pat. No. 5,427,798, comprising a sustained release tablet which provides peak bupropion blood levels at approximately 2–3 hours, thereby requiring twice daily dosing. Controlled release is achieved by combining bupropion particles with microcrystalline cellulose and hydrogel-forming hydroxypropyl methylcellulose.

Another sustained release bupropion tablet or caplet formulation disclosed in U.S. Pat. No. 4,687,660, comprises a difficult manufacturing process and limited shelf-life. U.S. Pat. No. 5,358,970 discloses a formulation of bupropion hydrochloride which contains an acidic stabilizer.

U.S. Pat. No. Re 33,994 discloses a tablet formulation of a water insoluble, water-permeable film coating surrounding the drug core and a particulate, water-soluble, pore-forming material dispersed within the film coating; this osmotic gradient and channel forming system is applicable for tablet dosage forms. However, here also at least twice daily dosing is necessitated by the release profile of 25–70% of bupropion within 4 hours, and 40–90% within 6 hours. Wellbutrin® SR is a commercially available twice a day dosage form of bupropion which contains carnuba wax, cysteine hydrochloride, hydroxypropyl methylcellulose, magnesium stearate, microcrystalline cellulose, polyethylene glycol and titanium dioxide.

There is no capsule formulation of bupropion commercially available. Capsules are advantageous in those patients who have difficulty swallowing where the contents of the capsule may be sprinkled on food.

Immediate release tablets must be stored at a temperature above 15–25° C. and protected from light and moisture. Extended-release tablets should be stored in tight, light resistant containers at a temperature of 20–25° C.

The need exists for a delayed, sustained release pharmaceutical preparation which provides a longer delay of drug dissolution thereby allowing greater flexibility in designing sustained release profiles, provides improved plasma levels wherein the maximum plasma concentration ($C_{max}$) can be substantially reduced without a concomitant reduction in AUC, and is simply and economically produced. Such a delayed delivery dosage form has a practical application, and it represents a valuable contribution to the medical arts. The present invention provides such a composition, and offers an efficient and cost effective method of preparation.

Accordingly, it is an object of this invention to provide a sustained release formulation of bupropion suitable for once daily administration.

Another object of the present invention is to provide a capsule dosage form comprising means for delaying delivery of the drug for 6 hours up to 12 hours from a dosage form, usually 4 hour to 8 hours.

It is also an object of this invention to provide a controlled and extended release bupropion capsule formulation that is easy to manufacture and can be used to prepare a range of dosing levels suitable for once daily administration.

It is a further object of the present invention to provide 24 hour control of symptoms of depression or tobacco dependence withdrawal.

Seizures result more commonly by single dosages of bupropion over 150 mg, hence the need for twice to four times daily dosing regimens. Another object of this invention is to provide a simplified once daily dosing regimen with the potential to prevent or reduce the incidence of seizures caused by bupropion.

The present invention also relates to a new sustained release bupropion pharmaceutical composition producing novel blood plasma levels after ingestion over 24 hours which is not disclosed in, not rendered obvious by, said patents nor elsewhere in the art. Other objects, features and advantages of the invention are not taught in the prior art but will be more apparent to those versed in the art from the following specification, taken in conjunction with the drawings.

SUMMARY OF THE INVENTION

The present invention meets the unfulfilled needs of the pharmaceutical industry.

The current invention involves a new pelletization process, typified by the application of a bupropion/cellulose ether suspension to inert spheres and two unique formulations of sustained release coating which are applied to separate active drug pellets. The formulation functions by membrane-controlled extended-release in a pH dependent manner. The bupropion release rate has been improved by the introduction of uncoated bupropion and two types of film coated active pellets which release the drug at different pH resulting in novel dissolution profiles.

Inert spheres are initially coated with bupropion and hydroxypropyl methylcellulose. These active pellets can be directly employed as the first component of the formulation of the present invention. Alternatively, loose bupropion granules may be employed. An enteric coating, applied to from about 10 to about 90 weight percent of the active drug pellets, is comprised of film insoluble at low pH comprising hydroxypropyl methylcellulose phthalate. The second coating applied to from about 90 to about 10 weight percent of active drug pellets is comprised of a combination of a hydrophobic coating agent and a methyl acrylate ester copolymer. The three components are then combined in a capsule. Generally, the weight ratio of the first component to the second component may vary from about 1:50 to about 50:1, the weight ratio of the first component to the third component may vary from about 1:50 to about 50:1, and the weight ratio of the second component to the third component may vary from about 10:90 to about 90:10, although a weight ratio of from about 30:70 to about 70:30 is preferred. Especially preferred is a weight ratio of three components of about 10:30:60.

This formulation can provide 24 hour efficacy with once-daily dosing, with less than 50% of drug released at 10 hours. Therapeutic plasma levels are maintained from 12 to 24 hours. The usual dosage range is 75–450 mg.

DETAILED DESCRIPTION OF THE INVENTION

Figure 1:
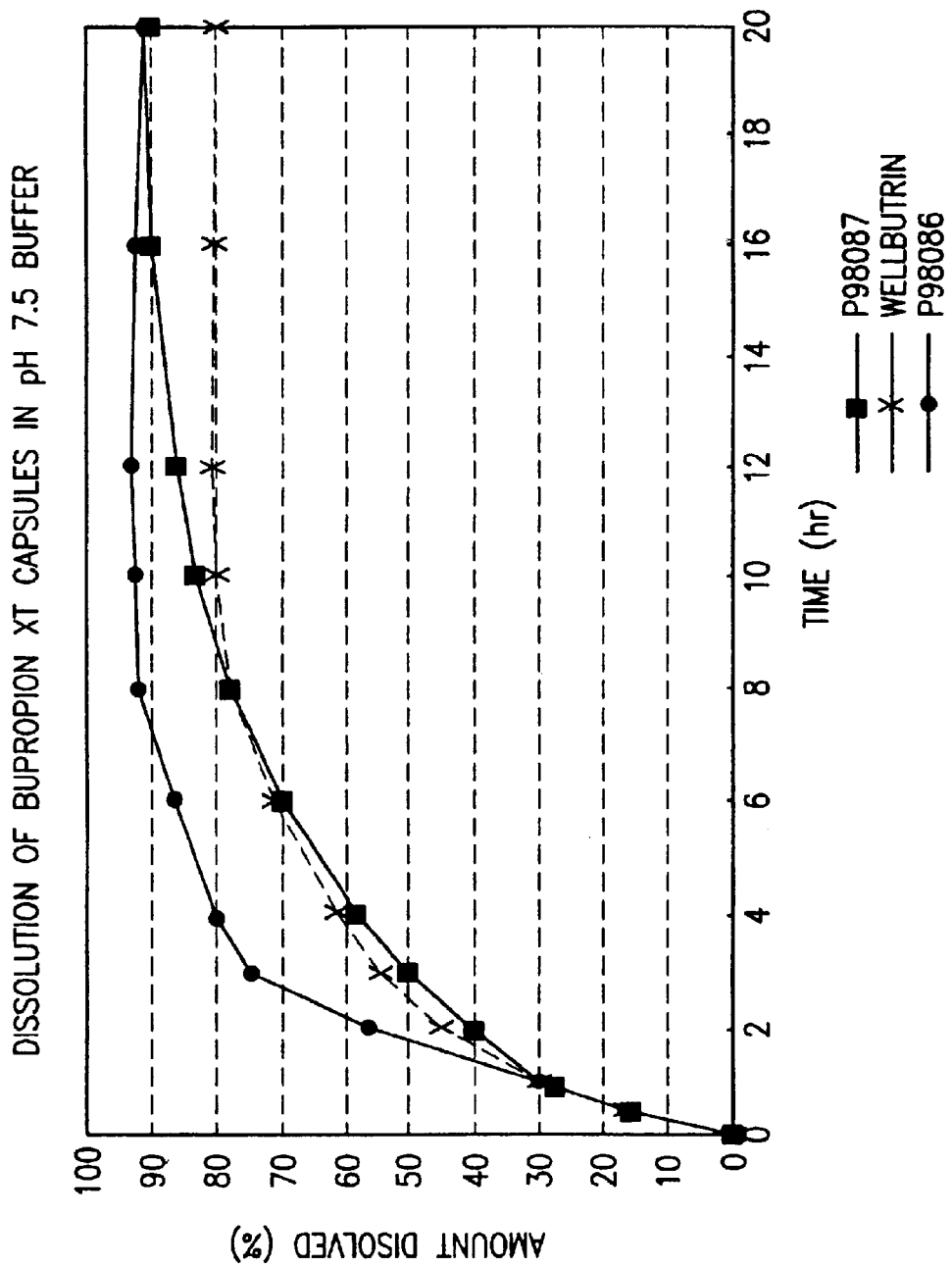
FIG. 1 is a graph depicting the dissolution profile in a pH 7.5 buffer of the formulations as described in Examples 1A and 2A versus the dissolution of the commercially available form of bupropion (Wellbutrin®SR).

The invention provides a controlled release bupropion formulation for oral administration, said formulation comprising:
(1) a first component comprising immediate release bupropion;
(2) a second component in the form of pellets comprising:
 (i) a core comprising:
  (a) bupropion and its salts, isomers, or a pharmaceutically acceptable aminoketone antidepressant agent;
  (b) an inert pellet as a starting material; and
  (c) a binder; and
 (ii) a coating comprising;
  (a) a pH dependent coating agent;
  (b) a plasticizer; and
  (c) a lubricant; and (3) a third component in the form of pellets comprising:
   (i) a core comprising:
      (a) bupropion and its salts, isomers, or a pharmaceutically acceptable aminoketone antidepressant agent;
      (b) an inert pellet as a starting material; and
      (c) a binder; and
   (ii) a coating comprising:
      (a) a water insoluble methyl acrylic acid copolymer;
      (b) a water soluble polymer;
      (c) a plasticizer; and
      (d) an antisticking agent.

The first component of the present invention may comprise any form of immediate release bupropion. This may take the form of uncoated bupropion granules or powder, may comprise bupropion active pellets (as described hereinbelow) or may include bupropion granules or active pellets coated with a highly soluble immediate release coating, such as an Opadry type coating, as are known to those skilled in the art. See generally, U.S. Pat. No. 5,098,715.

The active pellets of bupropion hydrochloride useful in the practice of the present invention are preferably based on active pellets having a core forming inert component which may comprise any type of commonly known pellet starting material such as starch or sugar spheres having a diameter ranging from about 15 to about 50 mesh, preferably from about 30 to about 35 mesh. The preferred pellet starting material is sugar spheres, NF containing not less than about 62.5 percent and not more than about 91.5 percent of sucrose. The spheres should have consistent bulk density, low friability, and low dust generation properties.

The inert core is preferably coated with an aminoketone antidepressant agent or a pharmaceutically acceptable derivative salt or stereoisomer thereof. Most preferably, the core drug is bupropion hydrochloride.

The core forming inert component is coated with a formulation which comprises bupropion hydrochloride and a binding agent. The binding agent should be water soluble, and should possess high adhesivity and an appropriate viscosity, to guarantee good adhesion between the sugar cores and bupropion particles, resulting in a high concentration of drug in the pellets. The binding agents employed can be any type of binding agent commonly known in the art such as polyvinyl pyrrolidone, hydroxyethyl cellulose, hydroxypropyl cellulose, low molecular weight hydroxypropyl methylcellulose (HPMC), polymethacrylate or ethylcellulose. In a preferred embodiment of the present invention, the binding agent is a water soluble polymer such as hydroxypropyl methylcellulose having a viscosity in the range of 2–12 cps at 20° C., preferably 4–6 cps, such as the material sold as Methocel® E5. A preferred composition of the binder for bupropion is about 2–10% w/w, and most preferably 3–5%.

The active pellets of the present invention will preferably comprise the following ingredients:

| INGREDIENT | PREFERRED | MOST PREFERRED |
| --- | --- | --- |
| bupropion | 40–80% | 60–70% |
| HPMC | 2–10% | 2.5–5% |
| starting pellets | 10–35% | 15–30% |

All the percentages in the above table are based on the total weight of the core.

The active pellets for use in the practice of the present invention which comprises the bupropion are prepared by forming a suspension of the binder and the drug and then layering the suspension onto the starting pellet using any of the layering techniques known in the industry such as fluidized bed coating, rotor granulation or pan coating. The suspension medium may comprise any low viscosity solvent such as isopropyl alcohol, ethanol, water, mixtures thereof and the like. A sufficient amount of coating is applied to provide the desired dosage of bupropion. These active pellets may be used directly as the first component of the formulation of the present invention.

The active pellets for use in forming the second and third components of the present invention are divided into two groups, each group receiving a film coating which releases the drug at a different pH. One group of pellets is film coated to release drug at a pH corresponding to about 4.8 and lower which is likely to occur in the upper GI tract; the other group of pellets is film coated to release drug at a pH of 7 and above which is likely to occur in the lower GI tract. Thus, the entire dose is released from this product for an extended period of time during its transition through the GI tract.

In a preferred embodiment, the first group of pellets is film coated with a film comprising a pH dependent coating polymer, a plasticizer and a lubricant. This group of pellets preferably comprises from about 10 to about 90 weight percent of the total pellets, preferably from about 30 to about 70 weight percent, and most preferably from about 33 to about 60 wt %.

The pH dependent coating polymer may be selected from those enteric coatings known to those skilled in the art. Preferably, the pH dependent coating is selected from the group consisting of shellac, methacrylic acid copolymers, cellulose acetate phthalate, hydroxypropyl methylcellulose phthalate, hydroxypropyl methylcellulose acetate succinate, cellulose acetate trimellitate, polyvinyl acetate phthalate or mixtures thereof. Hydroxypropyl methylcellulose phthalate (HPMCP) is preferred. The preferred concentration is 2–10% w/w of the total dosage form, and most preferably 3–5%.

The coating preferably also contains plasticizers. Plasticizers which may be used include any of those known to those skilled in the art, including but not limited to, acetyltributyl citrate, triacetin, acetylated monoglyceride, rape oil, olive oil, sesame oil, acetyltriethyl citrate, glycerin sorbitol, diethyloxalate, diethylmalate, diethylfumerate, dibutylsuccinate, diethylmalonate, dioctylphthalate, dibutylphthalate, dibutylsebacate, triethyl citrate, tributylcitrate, glyceroltributyrate, polyethylene glycol, propylene glycol and mixtures thereof. The preferred plasticizer is acetyltributyl citrate in an amount ranging from about 1 to about 15 percent based on the total weight of the final coating or 0.1–3% w/w of the total dosage form.

The coating further preferably includes a lubricant such as those selected from the group consisting of glyceryl monostearates; Myvaplex 600P, calcium stearate or stearic acid. The preferred lubricant is glycerol monostearate in an amount ranging from about 1 to about 15 percent, and most preferably 1–2.5%, based on the total weight of the coating.

This coating which comprises one third of the capsule content is preferably comprised of the following ingredients:

| INGREDIENT | PREFERRED | MOST PREFERRED |
|---|---|---|
| HPMCP | 2–10% | 3–5% |
| Acetyltributyl citrate | 0.1–3% | 0.5–1% |
| Glyceryl monostearate | 1–3% | 1–2.5% |

Additional active drug pellets for forming the second component of the present invention, preferably from about 90 to about 10 weight percent of the total pellets, more preferably from about 70 to about 30 weight percent, and most preferably from about 67 to about 40 weight percent, are coated with a coating which comprises a water-insoluble polymer such as methacrylic acid copolymer, a water soluble polymer, a plasticizer, and an anti-sticking agent.

The anti-sticking agent can be chosen from any of the known agents such as those selected from the group consisting of an alkaline earth metal stearate, such as magnesium stearate or calcium stearate, or talc. The antisticking agents can be used alone or in combination in effective amounts. The preferred anti-sticking agent is talc.

The water insoluble methacrylic acid copolymer is selected from the group of water insoluble methacrylic acid copolymers, preferably Eudragit S, and most preferably Eudragit S100. The preferred concentration is 1–15% of the total weight of the dosage form, preferably 4–7%.

The water soluble polymer in the preferred embodiment is formed from a cellulose ester, or a cellulose ester-ether. Representative materials include a member selected from the group consisting of ethyl cellulose, cellulose acylate, cellulose deacylate, cellulose triacylate, cellulose acetate, cellulose diacetate, cellulose triacetate, mono- di- and tri-cellulose arylates, and the like. Preferred is ethyl cellulose in a concentration ranging from 1–20%, preferably 2–13%.

The plasticizer additive for the second coating may be selected from any of those mentioned above in effective amounts. Acetyltributyl citrate is preferred.

The coatings for the active pellets are applied by forming a solution of the respective coating in a solvent such as acetone and isopropyl alcohol and employing any of the application techniques known to those skilled in the art, such as fluidized bed coating, rotor granulation or pan coating.

The three components of the present invention are blended together in the desired ratio to obtain a finished product and placed in a gelatin capsule. By varying the ratios of the three components, novel dissolution profiles and plasma profiles may be obtained. Alternatively, they may be made into tablets by first adding from 25 to 40 wt % of a solid pharmaceutically acceptable tablet excipient which will form a compressible mixture without crushing the pellets.

The following examples illustrate the present invention and are not intended to limit the scope of the present invention.

Comparative Example 1A

A batch of the controlled release bupropion was manufactured using all materials which comply with the current USP/NF compendial specifications.

A controlled release 150 mg oral bupropion dosage form is prepared by forming active core pellets having the following composition:

I Active Core Pellets

| bupropion HCL | 70% |
|---|---|
| sugar sphere 30/35 | 26.5% |
| methocel E5 | 3.5% |

Active pellets of bupropion are formed by dissolving 2.8 kg of bupropion HCL and 0.140 kg of hydroxypropyl methylcellulose [Methocel E5] in a mixture of water and isopropyl alcohol. The active drug solution is then sprayed onto 1.06 kg of sugar spheres 30/35 in a fluidized bed processor with a Wuster insert. The active core pellets are then dried in a fluidized bed processor until the loss on drying is below 1%. The bupropion pellets are then passed through a 16 mesh screen and a 30 mesh screen and pellets are collected that are smaller than 16 mesh and larger than 30 mesh.

II. First Film Coating

| bupropion active pellets | 75% |
|---|---|
| HPMCP 50 | 16.9% |
| acetyltributyl citrate | 2.5% |
| myvaplex 600P | 5.6% |

For a group of about one-third of the pellets, 0.270 kg of hydroxypropyl methylcellulose phthalate and 0.040 kg of acetyltributyl citrate are dissolved in a mixture of purified water and isopropyl alcohol, USP. Then 0.090 kg of glyceryl monostearate [Myvaplex 600P] is dissolved into the solution above. The solution is then sprayed onto 1.2 kg of the bupropion core pellets in a fluidized bed processor with a Wuster insert. The pellets are then dried until the loss on drying (LOD) is less than 1%. The pellets are then mixed with 2% (w/w) talc for 10 minutes in a V-blender. The pellets are then passed through a 14 mesh screen and a 24 mesh screen and pellets that are smaller than 14 mesh and larger than 24 mesh are collected.

II. Film Coating for Second Group of Active Pellets

LOT P98086

(S100/EC=9:1)

| bupropion active pellets | 80% |
|---|---|
| eudragit S100 | 12.6% |
| ethocel 10 cps | 1.4% |
| acetyltributyl citrate | 2.0% |
| talc | 4.0% |

For another group of about two-thirds of the pellets, a coating is prepared where the ratio of the methacrylic acid copolymer to ethylcellulose is about 9:1. The coating is made as follows: 0.378 kg of methacrylic acid copolymer [Eudragit S100], 0.042 kg of ethylcellulose [Ethocel 10 cps], and 0.060 kg of acetyltributyl citrate are dissolved in a mixture of 0.690 kg acetone and 6.210 kg isopropyl alcohol. 0.120 kg of talc is then dispersed into the solution above. The suspension is then sprayed onto 2.40 kg of the active bupropion core pellets in a fluidized bed processor with a Wuster insert. The bupropion pellets are dried in a fluidized bed processor until the LOD is less than 1%. The pellets are mixed with 2% (w/w) talc for 10 minutes in a V-blender and passed through a 14 mesh screen and 24 mesh screen. Pellets smaller than 14 mesh and larger than 24 mesh are collected.

These pellets have the following coating composition:

| INGREDIENT | MG/CAPSULE | % TOTAL WT |
|---|---|---|
| Eudragit S100 | 22.5 | 6.4 |
| ethylcellulose, NF, 10 cps | 2.5 | 0.7 |
| acetyltributyl citrate | 3.6 | 1.0 |
| talc, USP | 7.1 | 2.0 |

The first group of pellets and the 9:1 above pellets are mixed after loading each group into dosators. The strength of the final product is 150 mg of bupropion with 50 mg of active drug in the first group of pellets and 100 mg of active drug in the second group. The pellets are then encapsulated into size "1" light turquoise blue/light turquoise blue capsules. The total weight of the formulation (capsule+pellets) is 350 mg.

The resulting bupropion capsules of Example 1 were then tested according to the USP XXIII dissolution test (type 2, basket) at 50 rpm, at 37° C. in pH 7.5 buffer and found to have the following release profile:

TABLE 1

| Time (hours) | % Released |
|---|---|
| 1 | 25 |
| 2 | 60 |
| 3 | 75 |
| 4 | 80 |
| 6 | 88 |
| 8 | 93 |
| 10 | 93 |
| 12 | 94 |
| 14 | 94 |
| 16 | 94 |

The release profile of the controlled release product shown in this Example is shown in FIG. 1 by the line with the filled in circles.

The bupropion capsules of Example 1A were then tested according to the USP XXIII dissolution test (type 2, basket) at 50 rpm, at 37° C. in SGF (pH 1.5) to determine the percent of the drug dissolved versus time:

TABLE 2

| Time (hrs) | Amt Dissolved |
|---|---|
| 1 | 0 |
| 2 | 1 |
| 3 | 2 |
| 4 | 3 |
| 6 | 7 |
| 8 | 15 |
| 10 | 30 |
| 12 | 45 |
| 14 | 50 |
| 16 | 56 |
| 20 | 60 |

Figure 2:
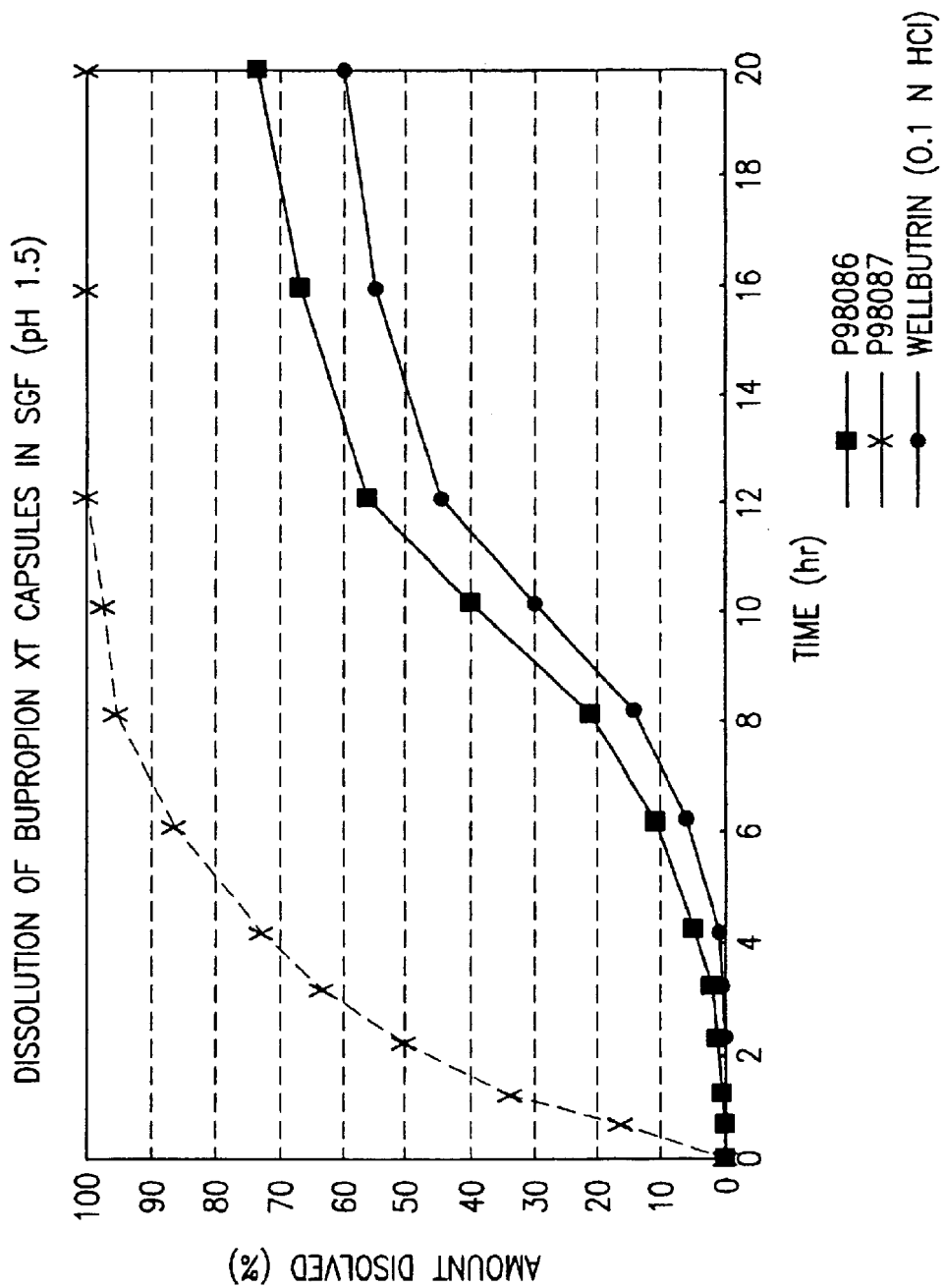
FIG. 2 is a graph depicting the dissolution profile in simulated gastric fluid (pH 1.5) of the formulations as described in Examples 1A and 2A versus the dissolution of the commercially available form of bupropion (Wellbutrin® SR).

The release profile of the controlled release product shown in this Example 1A is shown in FIG. 2 by the line with the filled in circles.

The bupropion capsules of Example 1A were then analyzed in a seven patient test using standard techniques known in the art. Bupropion was first detected in the plasma at about 2 hours after administration, and showed sustained release over 24 hours.

Two panels of seven patients were randomly assigned to receive either the bupropion formulation described herein or ZYBAN® in an open, randomized single dose study. Blood samples were collected over a 72 hour period and analyzed for bupropion concentrations with a LC/MS/MS method.

Figure 3:
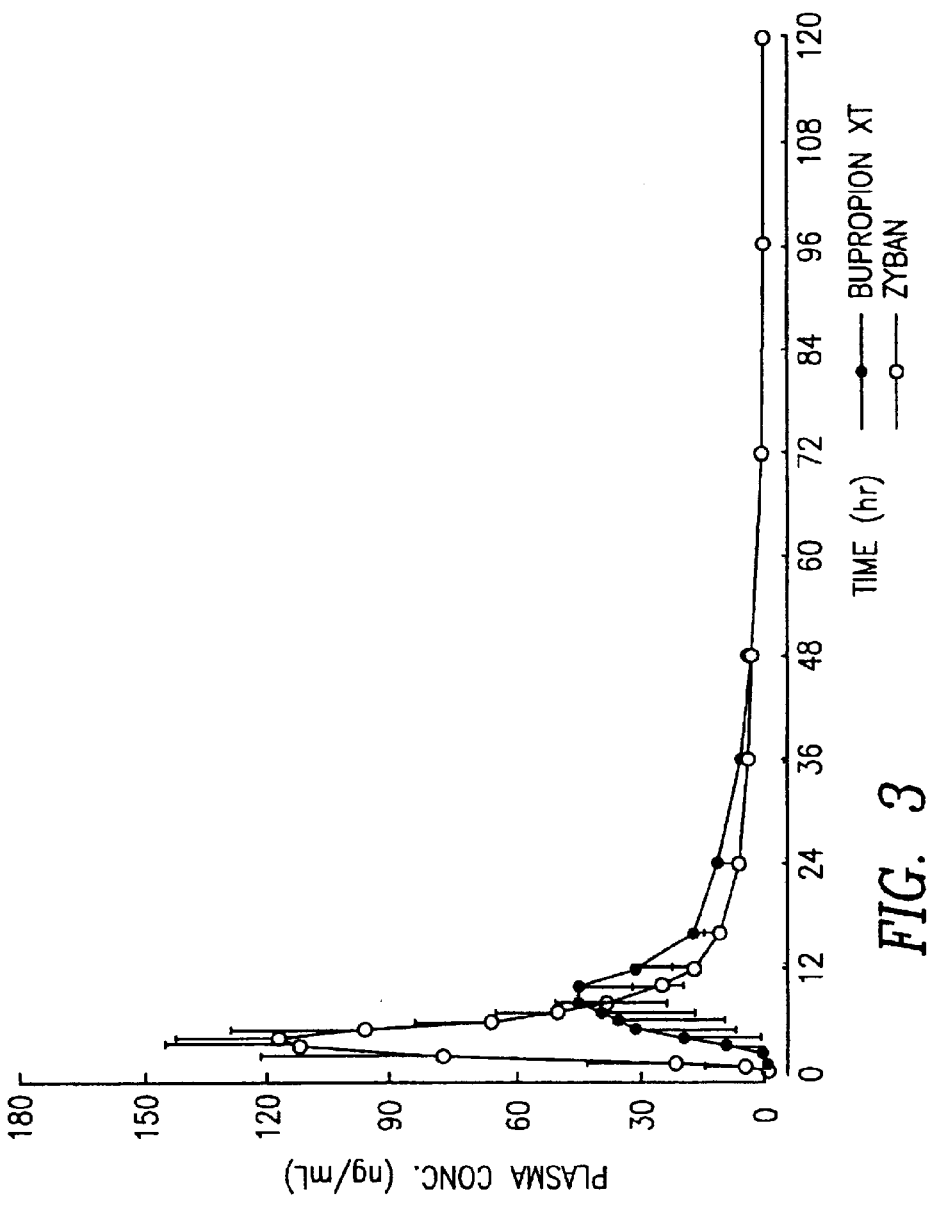
FIG. 3 is a graph depicting the mean plasma concentration-time profiles of bupropion in seven healthy subjects (smokers) following a single oral dose of the formulation in Example 1A versus 150 mg of the commercially available sustained release product (Zyban®).

For the blood levels carried out $C_{max}$ is the maximum blood level concentration of bupropion, $T_{max}$ is the time at which the maximum blood level concentration occurs, $T_{lag}$ is the sampling point preceding the one at which plasma concentrations first became quantifiable. AUC is the "area under the curve" of time versus blood concentration. The results provided are given in Table 3 and FIG. 3 and show that the mean plasma concentration-time profiles of bupropion were different for bupropion and ZYBAN®. Following oral administration, the bupropion formulation had a delayed absorption with a $T_{lag}$ value of 1.9 hours. The mean $C_{max}$ value of bupropion was about one-half of that following ZYBAN®. The time to reach $(T_{max})$ maximum plasma concentration occurred about 8 hours after administration of the bupropion formulation. The relative bioavailability of bupropion to ZYBAN® was 40% in terms of $C_{max}$ ratio and 80% in terms of $AUC_{0-inf.}$ ratio.

TABLE 3

|  | Test Mean | Ref. Mean | G-Mean Ratio |
|---|---|---|---|
| $C_{max}$ (ng/ml) | 54.2 | 129.0 | 0.40 |
| $AUC_{0-inf.}$ | 832.0 | 998.0 | 0.80 |
| $T_{lag}$ | 1.9 | 0.1 |  |
| $T_{max}$ | 8.1 | 3.6 |  |
| $T_{1/2}$ | 17.0 | 20.3 |  |

Thus, it can be seen from the above-data that although the $C_{max}$ has been significantly reduced, the AUC has only been slightly reduced, as compared to the reference product.

EXAMPLE 1

The pellets from Comparative Example 1A are taken as the second and third components. These pellets are loaded into the dosator along with active pellets and are filled into capsules in a ratio of 10:30:60 while maintaining the dosage at 150 mg. The blood profiles from this example will show a $C_{max}$ the same as in Table 3, but will show a slightly increased AUC, thereby rendering the G-Mean ratio at about 1.00. The amount of active pellets may be adjusted as is known to those skilled in the art without undue experimentation in order to substantially provide a G-Mean for AUC of approximately 1.00.

Comparative Example 2A

Proceed as in Example 1A for a first group of pellets. The core of the present invention which comprises bupropion is prepared by forming a suspension of bupropion and hydroxypropyl methylcellulose in a mixture of water and isopropyl alcohol and coating the suspension onto inert spheres. The HPMC phthalate coating as in Example 1A is applied to about one third of the active drug pellets.

Film Coating for Second Group of Active Pellets

A second group of about two-thirds of the pellets a coating is prepared where the ratio of methacrylic acid copolymer to ethylcellulose is about 1:1. The pellets have the following composition:

LOT P98087

(S100/EC=1:1)

| | |
|---|---|
| bupropion active pellets | 80% |
| eudragit S 100 | 7.0% |
| ethocel 10 cps | 7.0% |
| acetyltributyl citrate | 2.0% |
| talc | 4.0% |

The coating is made as follows: 0.105 kg of methacrylic acid copolymer [Eudragit S100], 0.105 kg of ethylcellulose [Ethocel 10 cps], and 0.030 kg of acetyltributyl citrate are dissolved in a mixture of 0.345 kg acetone and 3.105 kg isopropyl alcohol. 0.060 kg of talc is then dispersed into the solution above. The suspension is then sprayed onto 1.20 kg of the active bupropion core pellets in a fluidized bed processor with a Wuster insert. The bupropion pellets are dried in a fluidized bed processor until the LOD is less than 1%. The pellets are mixed with 2% (w/w) talc for 10 minutes in a V-blender and passed through a 14 mesh screen and 24 mesh screen. Pellets smaller than 14 mesh and larger than 24 mesh are collected.

The pellets have the following coating composition:

| INGREDIENT | MG/CAPSULE | % TOTAL WT. |
|---|---|---|
| methacrylic acid coplymer | 12.5 | 3.6 |
| ethylcellulose, NF, 10 cps | 12.5 | 3.6 |
| acetyltributyl citrate | 3.6 | 1.0 |
| talc | 7.1 | 2.0 |

The first group of pellets and the 1:1 above pellets are mixed after loading each group into dosators. The strength of the final product is 150 mg of bupropion with 50 mg of active drug in the first group of pellets and 100 mg of active drug in the second group. The total weight of the formulation (capsule+pellets) is 352 mg. The pellets are then encapsulated into size "1" buff opaque/light blue opaque capsules.

The resulting bupropion capsules were then tested according to the USP XXIII dissolution test (type 2, basket), at 50 rpm, at 37° C., in pH 7.5 buffer and found to have the following release profile:

| Time (hours) | % Released |
|---|---|
| 1 | 28 |
| 2 | 40 |
| 3 | 50 |
| 4 | 58 |
| 6 | 70 |
| 8 | 80 |
| 10 | 83 |
| 12 | 87 |
| 14 | 88 |
| 16 | 90 |
| 18 | 90 |
| 20 | 92 |

The release profile of the controlled release product shown in this Example 2A is shown in FIG. 1 by the line with the filled in squares.

The resulting bupropion capsules were then tested according to USP XXIII dissolution test (type 2, basket), at 50 rpm, at 37° C., in SGF (pH 1.5) and found to have the following release profile:

| Time (hours) | % Released |
|---|---|
| 1 | 0 |
| 2 | 2 |
| 3 | 4 |
| 4 | 6 |
| 6 | 12 |
| 8 | 21 |
| 10 | 40 |
| 12 | 57 |
| 14 | 64 |
| 16 | 68 |
| 18 | 71 |
| 20 | 74 |

The release profile of the controlled release product shown in this Example 2A is shown in FIG. 2 by the line with the filled in squares.

Bupropion capsules, such as those produced in Example 2A, were analyzed in a seven patient test using techniques known in the art. Bupropion was first detected in the plasma about 1.4 hours after administration, and showed a sustained release over 24 hours.

Figure 4:
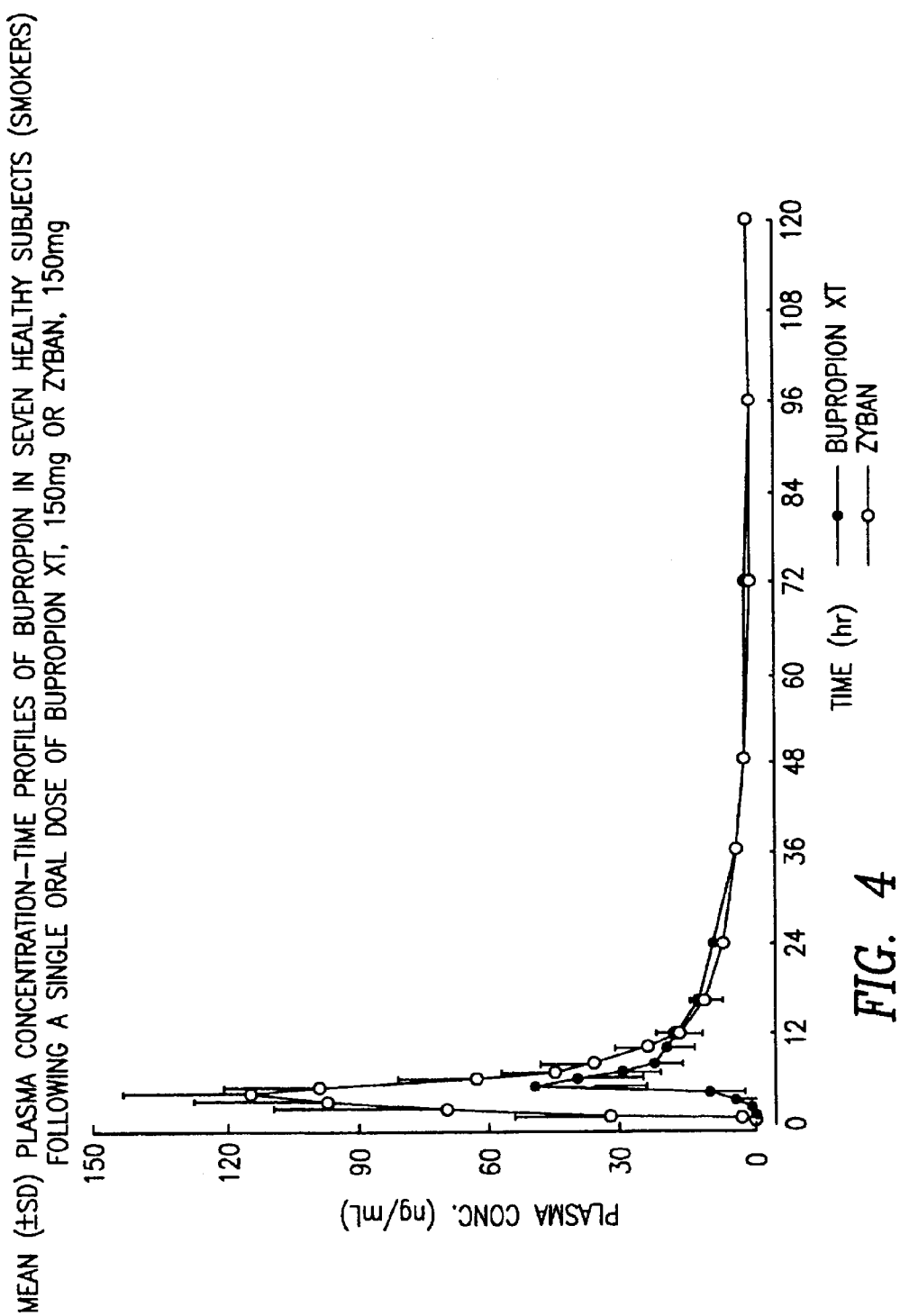
FIG. 4 is a graph depicting the mean plasma concentration-time profiles of bupropion in seven healthy subjects (smokers) following a single oral dose of the formulation in Example 2A versus 150 mg of the commercially available sustained release product (Zyban®).

The procedure is as described in Example 1A. The results provided are given in Table 4 and FIG. 4 and show that the mean plasma-time profile of the bupropion formulation differs from that of ZYBAN®. Bupropion had a delayed absorption, the relative bioavailability of bupropion to ZYBAN® was 48% and 59% in terms of $C_{max}$ and AUC values, respectively. The terminal elimination half-lives were similar.

TABLE 4

| | Test Mean | Ref. Mean | G-Mean Ratio |
|---|---|---|---|
| $C_{max}$ (ng/ml) | 56.9 | 114.8 | 0.48 |
| $AUC_{0-inf.}$ | 531.7 | 889.5 | 0.59 |
| $T_{lag}$ | 1.4 | 0.1 | |
| $T_{max}$ | 5.1 | 4.1 | |
| $T_{1/2}$ | 12.6 | 14.1 | |

Thus, again the $C_{max}$ was reduced significantly more than the AUC compared to the reference product demonstrating that an effective once-a-day product has been provided.

EXAMPLE 2

The pellets from Comparative Example 2A are taken as the second and third components. These pellets are loaded into the dosator along with active pellets and are filled into capsules in a ratio of 10:30:60 while maintaining the dosage at 150 mg bupropion. The blood profiles from this example will show a $C_{max}$ the same as in Table 3, but will show a slightly increased AUC, thereby rendering the G-Mean ratio at about 1.00. The amount of active pellets may be adjusted as is known to those skilled in the art without undue experimentation in order to substantially provide a G-Mean for AUC of approximately 1.00.

While certain preferred and alternative embodiments of the invention have been set forth for purposes of disclosing the invention, modifications to the disclosed embodiments may occur to those who are skilled in the art. Accordingly, this specification is intended to cover all embodiments of the invention and modifications thereof which do not depart from the spirit and scope of the invention.

What is claimed is:

1. A controlled release bupropion formulation comprising:
   (a) a first component comprising immediate release bupropion and its salts, isomers or a pharmaceutically acceptable aminoketone antidepressant;
   (b) a second component comprising pellets comprising:
      (i) a core comprising (1) an inert carrier, (2) bupropion and its salts, isomers, or a pharmaceutically acceptable aminoketone antidepressant agent; and (3) a binder; and
      (ii) a coating comprising a pH dependent coating agent; and
   (c) a third component comprising pellets comprising:
      (i) a core comprising (1) an inert carrier, (2) bupropion and its salts, isomers, or a pharmaceutically acceptable aminoketone antidepressant agent; and (3) a binder; and
      (ii) a coating comprising (I) a water insoluble methyl acrylic acid copolymer and (II) a water soluble polymer.

2. A controlled release bupropion formulation as defined in claim 1 wherein said immediate release component comprises an inert sugar sphere coated with a layer of binder and bupropion.

3. A controlled release bupropion formulation as defined in claim 2 wherein said immediate release component binder comprises hydroxypropyl methylcellulose.

4. A controlled release bupropion formulation as defined in claim 1 wherein said inert carrier comprises a sugar sphere.

5. A controlled release formulation as defined in claim 1 wherein said binder comprises hydroxypropylmethylcellulose.

6. A controlled release formulation as defined in claim 1 wherein said water insoluble methyl acrylic acid copolymer comprises Eudragit S100.

7. A controlled release formulation as defined in claim 1 wherein said water insoluble polymer comprises ethylcellulose.

8. A controlled release formulation as defined in claim 1 wherein said pH dependent coating comprises hydroxypropyl methylcellulose phthalate.

* * * * *